(12) United States Patent
Despande et al.

(10) Patent No.: US 10,479,787 B2
(45) Date of Patent: Nov. 19, 2019

(54) PROCESS FOR PREPARATION OF TETRABENAZINE AND DEUTETRABENAZINE

(71) Applicant: Lupin Limited, Mumbai (IN)

(72) Inventors: Tushar Nandkumar Despande, Pune (IN); Dnyaneshwar Tukaram Singare, Pune (IN); Yogesh Dadaji Pawar, Pune (IN); Yuvraj Atmaram Chavan, Pune (IN); Purna Chandra Ray, Pune (IN); Girij Pal Singh, Pune (IN)

(73) Assignee: Lupin Limited, Maharashtra (IN)

( * ) Notice: Subject to any disclaimer, the term of this patent is extended or adjusted under 35 U.S.C. 154(b) by 0 days.

(21) Appl. No.: 16/095,424

(22) PCT Filed: Apr. 12, 2017

(86) PCT No.: PCT/IB2017/052108
§ 371 (c)(1),
(2) Date: Oct. 22, 2018

(87) PCT Pub. No.: WO2017/182916
PCT Pub. Date: Oct. 26, 2017

(65) Prior Publication Data
US 2019/0135803 A1    May 9, 2019

(30) Foreign Application Priority Data
Apr. 22, 2016  (IN) .............................. 201621014182

(51) Int. Cl.
*C07D 455/06* (2006.01)

(52) U.S. Cl.
CPC ........ *C07D 455/06* (2013.01); *C07B 2200/05* (2013.01)

(58) Field of Classification Search
CPC ..................................................... C07D 455/06
USPC .......................................................... 546/95
See application file for complete search history.

(56) References Cited

U.S. PATENT DOCUMENTS

| 3,045,021 A | 7/1962 | Brossi |
| 8,524,733 B2 | 9/2013 | Gant et al. |
| 2015/0152099 A1 | 6/2015 | Zhang |

FOREIGN PATENT DOCUMENTS

| GB | 999095 A | 7/1965 |
| WO | 2008/058261 A1 | 5/2008 |
| WO | 2010/026436 A2 | 3/2010 |
| WO | 2015/112707 A1 | 7/2015 |

OTHER PUBLICATIONS

Ray; Org. Process Res. Dev. 2018, 22, 520-526. (Year: 2018).*
PCT International Search Report dated Jun. 27, 2017, Application No. PCT/IB2017/052108.

* cited by examiner

*Primary Examiner* — Daniel R Carcanague
(74) *Attorney, Agent, or Firm* — The Dobrusin Law Firm, PC

(57) ABSTRACT

The present invention provides process for preparation of dihydroxy benzoquinoline compound (III) comprising reacting dihydroxy isoquinoline compound (IV) or a salt thereof with (2-acetyl-4-methyl-pentyl)-trimethyl-ammonium iodide (V) and further converting it to tetrabenazine (I) and deutetrabenazine (II).

19 Claims, No Drawings

PROCESS FOR PREPARATION OF TETRABENAZINE AND DEUTETRABENAZINE

FIELD OF INVENTION

The present invention provides novel process for preparation of tetrabenazine and deutetrabenazine.

BACKGROUND OF THE INVENTION

Tetrabenazine (I) is a benzoquinoline compound and a vesicular monoamine transporter 2 (VMAT2) inhibitor commonly prescribed for the treatment of Huntington's disease. Deutetrabenazine (II) is a deuterated analog of tetrabenazine (I) which has improved pharmacokinetic properties when compared to the non-deuterated drug. Currently the New Drug Application (NDA) for deutetrabenazine has been accepted by the U.S. Food and Drug Administration (FDA) for the treatment of chorea associated with Huntington disease.

The carbon-hydrogen bonds of tetrabenazine (I) contain a naturally occurring distribution of hydrogen isotopes however increased levels of deuterium incorporation may produce a detectable Deuterium Kinetic Isotope Effect (DKIE) that could affect the pharmacokinetic, pharmacologic and/or toxicologic profiles of tetrabenazine in comparison with tetrabenazine having naturally occurring levels of deuterium.

The U.S. Pat. No. 3,045,021 discloses process for preparation of tetrabenazine (I) and U.S. Pat. No. 8,524,733 discloses deutetrabenazine (II).

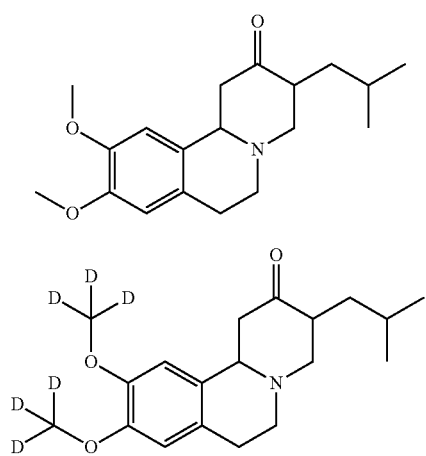

The U.S. Pat. No. 3,045,021, provides process for preparation of tetrabenazine (I) which comprises condensation of 6,7-dimethoxy-3,4-dihydroisoquinoline with 3-methylene-5-methyl-2-hexanone (VI) in an alkaline medium.

Another patent GB 999095 described process for preparation of tetrabenazine which involves reaction of 3,4-dihydro-6,7-dimethoxyisoquinoline and (2-acetyl-4-methyl-pentyl)-trimethyl-ammonium iodide (V) in alcohol.

The U.S. Pat. No. 8,524,733, provides process for preparation of deutetrabenazine by reaction of $d_6$-6,7-Dimethoxy-3,4-dihydroisoquinoline and (2-acetyl-4-methyl-pentyl)-trimethyl-ammonium iodide (V) in ethanol. The product is isolated by column chromatography in yield of 35%. The intermediate $d_6$-6,7-Dimethoxy-3,4-dihydroisoquinoline is prepared by series of reaction wherein (E)-4-(2-nitrovinyl)benzene-1,2-diol is reacted with $d_3$-Iodomethane to produce $d_6$-(E)-1,2-Dimethoxy-4-(2-nitrovinyl)benzene which undergoes reduction in presence of lithium aluminum hydride to give 2-(3,4-$d_6$-Dimethoxyphenyl)ethanamine which further reacts with hexamethylenetetramine in presence of acetic acid/trifluoroacetic acid to give the intermediate $d_6$-6,7-Dimethoxy-3,4-dihydroisoquinoline. The process utilizes expensive reagents like $d_3$-Iodomethane, tedious technique of column chromatography resulting in low yields hence is not industrially feasible.

Another patent application US 20150152099 describes process for preparation of deutetrabenazine by reaction of $d_6$-6,7-Dimethoxy-3,4-dihydroisoquinoline and (2-acetyl-4-methyl-pentyl)-trimethyl-ammonium iodide (V) in various solvents. The intermediate $d_6$-6,7-Dimethoxy-3,4-dihydroisoquinoline is prepared by series of reaction wherein dopamine hydrochloride reacts with ethyl formate to give N-(2-(3,4-dihydroxy-phenyl)-ethyl)-formamide which reacts further with $d_3$-Iodomethane to produce deuteriated compound which is cyclized in presence of phosphoryl chloride to give $d_6$-6,7-Dimethoxy-3,4-dihydroisoquinoline hydrochloride. The process utilizes expensive reagents like $d_3$-Iodomethane.

The present invention provides novel process for preparation of tetrabenazine (I) and deutetrabenazine (II) which is efficient, industrially viable and cost effective. The present invention provides novel process for preparation of deutetrabenazine (II) that does not involve tedious technique of column chromatography or expensive and non-commercially available $d_3$-Iodomethane.

SUMMARY OF THE INVENTION

The present invention provides novel process for preparation of tetrabenazine (I) comprising reacting dihydroxy isoquinoline compound (IV) or a salt thereof with (2-acetyl-4-methyl-pentyl)-trimethyl-ammonium iodide (V) or 3-methylene-5-methyl-2-hexanone (VI) to obtain dihydroxy benzoquinoline compound (III) followed by treatment with source of methyl. The present invention further provides novel process for preparation of deutetrabenazine (II) comprising reacting dihydroxy isoquinoline compound (IV) or a salt thereof with (2-acetyl-4-methyl-pentyl)-trimethyl-ammonium iodide (V) or 3-methylene-5-methyl-2-hexanone (VI) to obtain dihydroxy benzoquinoline compound (III) followed by treatment with source of deuteriated methyl.

DETAILED DESCRIPTION OF THE INVENTION

In the first embodiment the present invention provides process for preparation of dihydroxy benzoquinoline compound (III) which includes the step of:

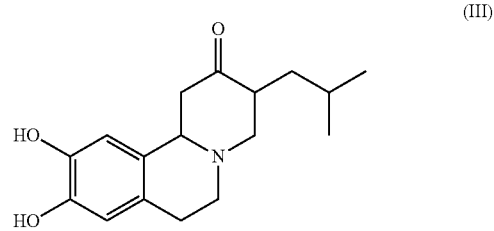 [SMILES: CC(C)CC1CN2CCc3cc(O)c(O)cc3C2CC1=O]

reacting dihydroxyisoquinoline compound (IV) or a salt thereof

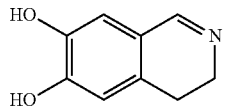

with (2-acetyl-4-methyl-pentyl)-trimethyl-ammonium iodide (V).

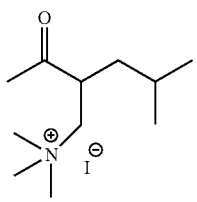

Salt of dihydroxy isoquinoline compound (IV) can be selected from inorganic salts such as hydrochloric, hydrobromic, sulfuric, phosphoric and the like.

In the second embodiment the present invention provides process for preparation of dihydroxy benzoquinoline compound (III) comprising reacting dihydroxy isoquinoline compound (IV) or a salt thereof with 3-methylene-5-methyl-2-hexanone (VI).

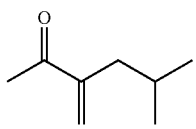

In the third embodiment the present invention provides process for preparation of tetrabenazine (I), comprising treating dihydroxy benzoquinoline compound (III) with source of methyl.

In the fourth embodiment the present invention provides process for preparation of deutetrabenazine (II), comprising treating dihydroxy benzoquinoline compound (III) with source of deuteriated methyl.

In the fifth embodiment the present invention provides process for preparation of tetrabenazine (I) comprising:
i) obtaining dihydroxy benzoquinoline compound (III) by reacting dihydroxy isoquinoline compound (IV) or a salt thereof with (2-acetyl-4-methyl-pentyl)-trimethyl-ammonium iodide (V) or 3-methylene-5-methyl-2-hexanone (VI)
ii) treating dihydroxy benzoquinoline compound (III) with source of methyl.

In the sixth embodiment the present invention provides process for preparation of deutetrabenazine (II) comprising:
i) obtaining dihydroxy benzoquinoline compound (III) by reacting dihydroxy isoquinoline compound (IV) or a salt thereof with (2-acetyl-4-methyl-pentyl)-trimethyl-ammonium iodide (V) or 3-methylene-5-methyl-2-hexanone (VI)
ii) treating dihydroxy benzoquinoline compound (III) with source of deuteriated methyl.

The reaction of dihydroxy isoquinoline compound (IV) or a salt thereof with (2-acetyl-4-methyl-pentyl)-trimethyl-ammonium iodide (V) can be carried out in presence of solvent and a base. The solvent can be selected from polar solvents like alcohols; alcohol can be selected from methanol, ethanol, propanol, butanol etc.; nitriles selected from acetonitrile, propionitrile etc.; acetone, tetrahydrofuran, dimethylformamide, dimethyl sulfoxide, glycol, dioxane, propanediol, butanediol, water or mixture thereof. The base can be selected from organic or inorganic base; organic base can be selected from alkyl amines like triethyl amine or tributyl amine etc. inorganic bases include hydroxide, alkoxides or carbonates, bicarbonates of alkali or alkaline earth metal like sodium hydroxide, potassium hydroxide, sodium methoxide, potassium methoxide, sodium carbonate, potassium carbonate, sodium bicarbonate etc. The reaction can be carried out at a temperature of 20 to 60 éC.

The reaction of dihydroxy isoquinoline compound (IV) or a salt thereof with 3-methylene-5-methyl-2-hexanone (VI) can be carried out in presence of solvent and a base. The solvent can be selected from polar solvents like alcohols; alcohol can be selected from methanol, ethanol, propanol, butanol etc.; nitriles selected from acetonitrile, propionitrile etc.; acetone, tetrahydrofuran, dimethylformamide, dimethyl sulfoxide, glycol, dioxane, propanediol, butanediol, water or mixture thereof. The base can be selected form organic or inorganic base; organic base can be selected form alkyl amines like triethyl amine or tributyl amine etc. inorganic bases include hydroxide, alkoxides or carbonates, bicarbonates of alkali or alkaline earth metal like sodium hydroxide, potassium hydroxide, sodium methoxide, potassium methoxide, sodium carbonate, potassium carbonate, sodium bicarbonate etc. The reaction can be carried out at a temperature of 20 to 60 éC.

The dihydroxy benzoquinoline compound (III) can be isolated by techniques known in art like filtration, evaporation, concentration etc. The dihydroxy benzoquinoline compound (III) is obtained in a HPLC purity of greater than 98.0%, preferably greater than 98.5%.

In the process of step (ii) for preparation of tetrabenazine (I), dihydroxy benzoquinoline compound (III) is treated with a source of methyl, selected form methanol, methoxy (diphenyl) phosphine, trimethoxy phosphine, trimethyl sulfonium hydroxide, dimethyl sulfate, dimethyl carbonate, methyl iodide, methyl bromide, methyl 2,2,2-trichloroacetate, morpholine, 4-methyl etc. The reaction can be carried out in solvents selected from nitriles like acetonitrile, propionitrile etc.; acetone, tetrahydrofuran, dimethylformamide, dimethyl sulfoxide, glycol, dioxane, propanediol, butanediol, or mixture thereof. In the process of step (ii) for preparation of tetrabenazine (I), wherein methanol is used as source of methyl, the reaction can be optionally carried out in presence catalyst selected from azodicarboxylate such as diethyl azodicarboxylate (DEAD) or diisopropyl azodicarboxylate (DIAD) and triphenyl phosphine. The reaction can be carried out at an ambient temperature of 5 to 30 éC.

Tetrabenazine (I) can be isolated by techniques known in art like filtration, evaporation, concentration etc. Tetrabenazine (I) obtained by this process is free from triphenyl phosphine and triphenyl phosphine oxide impurities.

In the process of step (ii) for preparation of deutetrabenazine (II), dihydroxy benzoquinoline compound (III) is treated with a source of deuteriated methyl selected from deuteriated methanol, deuteriated methoxy (diphenyl) phosphine, deuteriated trimethoxy phosphine, deuteriated trimethyl sulfonium hydroxide, deuteriated dimethyl sulfate, deuteriated dimethyl carbonate, deuteriated methyl iodide, deuteriated methyl bromide, deuteriated methyl 2,2,2-trichloroacetate, deuteriated morpholine, 4-methyl etc. In the process of step (ii) for preparation of deutetrabenazine (II), wherein deuteriated methanol is used as source of deuterated methyl, the reaction can be optionally carried out in presence of catalyst selected from azodicarboxylate such as diethyl azodicarboxylate (DEAD) or diisopropyl azodicarboxylate (DIAD) and triphenyl phosphine. In the reaction the mole ratio of source of deuterated methyl plays an important role. The mole ratio of source of deuterated methyl with respect to dihydroxy benzoquinoline compound (III) is greater than 2.5 moles. The reaction can be carried out in solvents selected from nitriles like acetonitrile, propionitrile; chlorinated hydrocarbon solvents like dichloromethane, ethylene dichloride, carbon tetrachloride, chloroform and other solvents selected from acetone, tetrahydrofuran, dimethylformamide, dimethyl sulfoxide, glycol, dioxane, propanediol, butanediol, or mixture thereof. The reaction can be carried out at an ambient temperature of 5 to 30 éC.

Deutetrabenazine (II) can be isolated by techniques known in art like filtration, evaporation, concentration etc. Isolated deutetrabenazine (II) was obtained in a HPLC purity of greater than 98.0%.

Deutetrabenazine (II) can be further recrystallized from solvents selected from esters like ethyl acetate, butyl acetate etc.; alcohols selected from methanol, ethanol, n-propanol, isopropanol, butanol etc.; nitriles selected from acetonitrile, propionitrile etc.; ketones selected from acetone, methyl isobutyl ketone etc., tetrahydrofuran, dimethylformamide, dimethyl sulfoxide, glycol, dioxane, propanediol, butanediol, water; non-polar solvents like toluene, hexane, heptane etc. or mixture thereof. Deutetrabenazine (II) obtained by this process is free from triphenyl phosphine and triphenyl phosphine oxide impurities and is highly pure. Deutetrabenazine (II) obtained by the present method has a HPLC purity of greater than 99.0%, preferably greater than 99.5%.

The present invention is further illustrated by the following representative examples and does not limit the scope of the invention.

EXAMPLES

Example 1: Preparation of Dihydroxy Benzoquinoline Compound (III)

A mixture of methanol (675 ml), dihydroxy isoquinoline compound (IV) hydrochloride (150 g) and water (225 ml) was stirred and (2-acetyl-4-methyl-pentyl)-trimethyl-ammonium iodide (V) (285 g) was added to it. The reaction mass was stirred at 25-30 éC and potassium carbonate (34.5 g) was added. The reaction mass was heated to 45-50 éC and was stirred for 30 hours. The reaction mass was cooled to 25-30 éC and water (450 ml) was added to it and stirred for 4 hours. The solid was filtered, washed with water and dried under vacuum. Yield: 138 g.

Example 2: Preparation of Dihydroxy Benzoquinoline Compound (III)

A mixture of methanol (12 L), dihydroxy isoquinoline compound (IV) hydrochloride (4.0 kg) and water (12 L) was stirred and (2-acetyl-4-methyl-pentyl)-trimethyl-ammonium iodide (V) (6.60 kg) was added to it. The reaction mass was stirred at 25-30 éC and potassium carbonate (2.8 kg) was added. The reaction mass was heated to 65-70 éC and was stirred for 30 hours. The reaction mass was cooled to 25-30 éC and water (12 L) was added to it and stirred for 4 hours. The solid was filtered and washed with water. The solid was taken up in isopropanol (10 L) and the mixture was heated to 75-80 é for 15-30 minutes. The reaction mass was cooled, the solid was filtered and washed with isopropanol and dried under vacuum Yield: 4.0 kg. HPLC purity: 98.6%.

Example 3: Preparation of Tetrabenazine (I)

To a mixture of tetrahydrofuran (2000 ml), dihydroxy benzoquinoline compound (III) (250 g), methanol (276.8 g) and triphenylphosphine (679.9 g) was added a solution of diisopropylazodicraboxylate (DIAD) (524.1 g) in tetrahydrofuran (500 ml) at 25-30 éC. The reaction mass was stirred for 3-6 hours at 25-30 éC. The reaction mass was concentrated under vacuum A mixture of water (2500 ml) and toluene (7500 ml) was added to the concentrated mass and the mixture was stirred. The aqueous layer was separated and the organic layer was washed with 5% aqueous sodium hydrogen sulphate solution (2500 ml, 3 times). The aqueous layers were collected together and the pH was adjusted to 9-11 using aqueous ammonia solution (750 ml). Dichloromethane (2500 ml) was added to it and the organic layer was separated and concentrated under vacuum. Water (1250 ml) was added to the concentrated mass and the mass was stirred for at 25-30 éC for 2 hours. The solid was filtered, washed with water and dried under vacuum Yield: 262.3 g.

Example 4: Purification of Tetrabenazine (I)

A mixture of tetrabenazine (I) (10 g) and ethyl acetate (30 ml) was heated to 65-70 éC. The mixture was stirred for 60-90 minutes and filtered through micron filter. The filtrate was cooled to 25-30 éC and n-heptane (100 ml) was added to it. The mixture was stirred for about 4 hours at 25-30 éC. The solid was filtered, washed with n-heptane and dried under vacuum Yield: 9.6 g.

Example 5: Preparation of Deutetrabenazine (II)

To a mixture of tetrahydrofuran (224 ml), dihydroxy benzoquinoline compound (III) (28 g), deuteriated methanol (34.9 g) and triphenylphosphine (76.1 g) was added a solution of diisopropylazodicraboxylate (DIAD) (58.7 g) in tetrahydrofuran (56 ml) at 25-30 éC. The reaction mass was stirred for 3-6 hours at 25-30 éC. The reaction mass was concentrated under vacuum. A mixture of water (280 ml) and toluene (840 ml) was added to the concentrated mass and the mixture was stirred. The aqueous layer was separated and the organic layer was washed with 5% aqueous sodium hydrogen sulphate solution (280 ml, 3 times). The aqueous layers were collected together and the pH was adjusted to 9-11 using aqueous ammonia solution. Dichloromethane (280 ml) was added to it and the organic layer was separated and concentrated under vacuum. Water (140 ml) was added to the concentrated mass and the mass was stirred for at 25-30 éC for 2 hours. The solid was filtered, washed with water and dried under vacuum. Yield: 29.4 g.

Example 6: Preparation of Deutetrabenazine (II)

To a mixture of dichloromethane (24 L), dihydroxy benzoquinoline compound (III) (3.0 kg), deuteriated methanol (3.75 kg) and triphenyl phosphine (8.16 kg) was added a solution of diisopropylazodicraboxylate (DIAD) (6.30 kg) in dichloromethane (6 L) at 25-30 éC. The reaction mass was stirred for 2 hours at 25-30 éC. The reaction mass was washed with water and the organic layer was concentrated under vacuum. Toluene was added to the residue and the mixture was stirred. The mixture was filtered and the filtrate was washed with 5% aqueous sodium hydrogen sulphate solution (15 L, 3 times). The aqueous layers were collected together and the pH was adjusted to 9-11 using aqueous ammonia solution. Dichloromethane (30 L) was added to it and the organic layer was separated and concentrated under vacuum Ethyl acetate (30 L) was added to the residue, carbon treatment was given and ethyl acetate was removed under vacuum. Isopropanol (6 L) was added to the residue and the mixture was heated to 75-80 éC for 15-30 minutes. The reaction mass was cooled, the solid was filtered and washed with isopropanol and dried under vacuum. Yield: 1.75 kg. HPLC purity: 98.5%.

Example 7: Purification of Deutetrabenazine (II)

A mixture of deutetrabenazine (II) (10 g) and ethyl acetate (30 ml) was heated to 65-70 éC. The mixture was stirred for 60-90 minutes and filtered through micron filter. The filtrate was cooled to 25-30 éC and n-heptane (100 ml) was added to it. The mixture was stirred for about 4 hours at 25-30 éC. The solid was filtered, washed with n-heptane and dried under vacuum. Yield: 9.6 g.

Example 8: Purification of Deutetrabenazine (II)

A mixture of deutetrabenazine (II) (1.70 kg) and ethyl acetate (13.6 L) was heated to 60-65 éC. The mixture was stirred for 60-90 minutes and filtered through micron filter. The filtrate was concentrated under vacuum and isopropanol (1.7 L) was added to the residue. The mixture was heated to 75-80 é for 15-30 minutes and then was cooled to 25-30 éC. The solid was filtered, washed with isopropanol and dried under vacuum. Yield: 1.53 kg. HPLC purity: 99.7%.

The invention claimed is:
1. A process for preparation of deutetrabenazine (II) comprising:

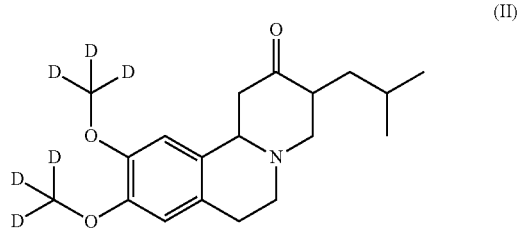 [SMILES: [2H]C([2H])([2H])Oc1cc2c(cc1OC([2H])([2H])[2H])C1CC(=O)C(CC(C)C)CN1CC2]
(II)

i) obtaining dihydroxy benzoquinoline compound (III)

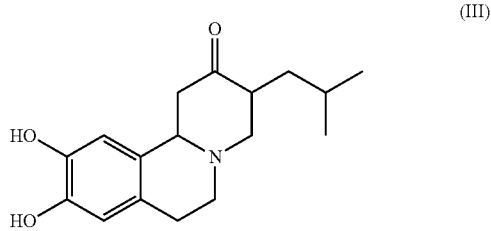 [SMILES: CC(C)CC1CN2CCc3cc(O)c(O)cc3C2CC1=O]
(III)

by reacting dihydroxy isoquinoline compound (IV) or a salt thereof

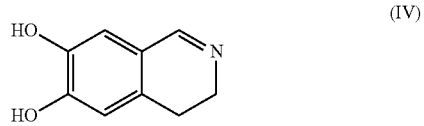 [SMILES: Oc1cc2c(cc1O)CCN=C2]
(IV)

with (2-acetyl-4-methyl-pentyl)-trimethyl-ammonium iodide (V) or 3-methylene-5-methyl-2-hexanone (VI), and

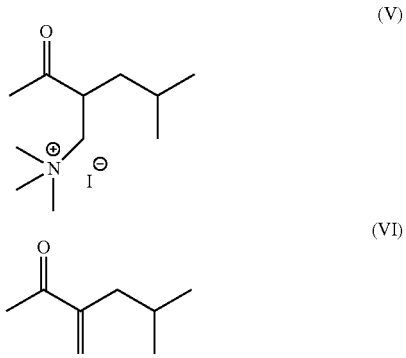

ii) treating dihydroxy benzoquinoline compound (III) with a source of deuteriated methyl, wherein the source of deuteriated methyl is deuteriated methanol.

2. The process according to claim 1, wherein the salt thereof of dihydroxy isoquinoline compound (IV) is selected from hydrochloric, hydrobromic, sulfuric or phosphoric.

3. The process according to claim 1, wherein step (i) is carried out in the presence of a solvent and a base.

4. The process according to claim 3, wherein the solvent is selected from alcohol, nitrile, acetone, tetrahydrofuran, dimethylformamide, dimethyl sulfoxide, glycol, dioxane, propanediol, butanediol, water or mixture thereof.

5. The process according to claim 4, wherein the solvent is an alcohol selected from methanol, ethanol, propanol or butanol.

6. The process according to claim 4, wherein the solvent is a nitrile selected from acetonitrile or propionitrile.

7. The process according to claim 3, wherein the base is selected from an organic or inorganic base.

8. The process according to claim 7, wherein the base is an organic base selected from alkyl amines.

9. The process according to claim 7, wherein the base is an inorganic base selected from hydroxide, alkoxides, carbonates or bicarbonates of alkali or alkaline earth metals.

10. The process according to claim 1, wherein step (ii) is carried out in solvents selected from nitriles, chlorinated hydrocarbon, acetone, tetrahydrofuran, dimethylformamide, dimethyl sulfoxide, glycol, dioxane, propanediol or butanediol.

11. The process according to claim 10, wherein the solvent is a nitrile selected from acetonitrile or propionitrile.

12. The process according to claim 10, wherein the solvent is a chlorinated hydrocarbon selected from dichloromethane, ethylene dichloride, carbon tetrachloride or chloroform.

13. The process according to claim 1, wherein step (ii) is optionally carried out in the presence of a catalyst selected from azodicarboxylate and triphenyl phosphine.

14. The process according to claim 13, wherein the catalyst is an azodicarboxylate selected from diethyl azodicarboxylate or diisopropyl azodicarboxylate.

15. The process according to claim 1, wherein the dihydroxy benzoquinoline compound (III) is obtained with HPLC purity of greater than 98.5%.

16. The process according to claim 1, further comprising recrystallization of deutetrabenazine (II) from a solvent.

17. The process according to claim 16, wherein the solvent is an ester or an alcohol.

18. The process according to claim 17, wherein the ester is ethyl acetate and the alcohol is isopropanol.

19. The process according to claim 16, wherein the deutetrabenazine (II) is obtained with HPLC purity of greater than 99.0%.

* * * * *